United States Patent [19]

Gutman

[11] 4,090,864
[45] May 23, 1978

[54] HERBICIDAL ACETAMIDOTHIOMETHYL UREAS

[75] Inventor: Arnold D. Gutman, Berkeley, Calif.

[73] Assignee: Stauffer Chemical Company, Westport, Conn.

[21] Appl. No.: 801,890

[22] Filed: May 31, 1977

[51] Int. Cl.$^2$ .................. A01N 9/12; C07C 127/15
[52] U.S. Cl. ............................. 71/98; 260/553 A
[58] Field of Search ................... 260/553 A; 71/98

[56] References Cited

U.S. PATENT DOCUMENTS

| | | | |
|---|---|---|---|
| 3,891,424 | 6/1975 | Brown et al. | 71/98 |
| 3,978,123 | 8/1976 | Chan | 260/553 A |
| 4,043,797 | 8/1977 | Arneklev et al. | 71/98 |
| 4,045,209 | 8/1977 | Hainaut et al. | 71/98 |

FOREIGN PATENT DOCUMENTS 2,601,051  7/1976  Germany ................ 260/553 A

Primary Examiner—Daniel E. Wyman
Assistant Examiner—Thomas A. Waltz
Attorney, Agent, or Firm—Michael J. Bradley

[57] ABSTRACT

Novel compounds are disclosed having the formula

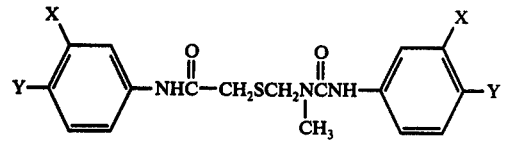

in which X and Y may be independently selected from the group consisting of hydrogen, chlorine, $CH_3$ and $CF_3$, which are useful as herbicides.

27 Claims, No Drawings

HERBICIDAL ACETAMIDOTHIOMETHYL UREAS

BACKGROUND OF THE INVENTION

Various substituted ureas are known to be useful as herbicides such as those taught in West German Pat. No. 2,256,275, U.S. Pat. No. 3,520,925 and U.S. Pat. No. 3,847,971. Compounds of the above cited patents are only remotely related to applicant's novel compounds because they are both derivatives of urea.

BRIEF DESCRIPTION OF THE INVENTION

This invention relates to novel acetamidothiomethyl ureas having the formula

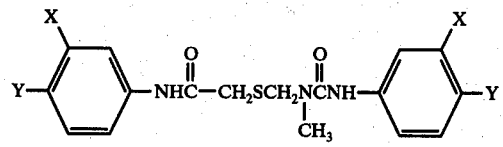

wherein X and Y may be independently selected from the group consisting of hydrogen, chlorine, $CH_3$ and $CF_3$. The compounds are useful as herbicides when used in a herbicidally effective amount.

The term "herbicides" as used herein means a compound which controls or modifies growth of plants. By the term "herbicidally effective amount" is meant an amount of compound which causes a modifying effect upon the growth of plants. By "plants" is meant germinant seeds, emerging seedlings and established vegetation, including roots and above-ground portions. Such modifying effects include all deviations from natural development; for example, killing, retardation, defoliation, desiccation, regulation, stunting, tillering, stimulation, leaf burn, dwarfing and the like.

The compounds of the present invention, as will be seen from the data which follows, have utility as both pre-emergence and post-emergency herbicides, against a wide range of plant species.

DETAILED DESCRIPTION OF THE INVENTION

The novel compounds of the present invention which are defined by the formula

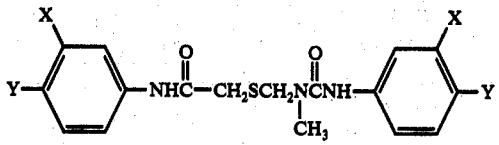

in which X and Y may be independently selected from the group consisting of hydrogen, chlorine, $CH_3$ and $CF_3$ and preferably are chlorine, which are useful as herbicides, exhibits herbicidal activity and are prepared by the following general reaction scheme:

(1) reacting in the presence of a solvent such as acetonitrile an appropriately substituted 1,3,5-hexa-hydro-s-triazine with mercapto acetic acid and hydrochloric acid gas at from about $-40°C$ to about $-20°C$ to produce an appropriately substituted amine salt, (2) recovering the amine salt from the solvent, (3) reacting the appropriately substituted amine salt with 2 molar equivalents of an appropriately 3,4 substituted phenyl isocyanate in the presence of at least 1 molar equivalent of an acid acceptor such as triethyl amine at room temperature in an inert solvent such as acetonitrile.

Although, the above reactions will proceed at any temperature, side reactions become more prominent at higher temperatures raising the level of impurities in the final product. For this reason, it is preferred to run the first reaction from about $-40°C$ to about $-20°C$ and most preferably at $-30°C$. It is preferred to run the second reaction at from about 20°C to about 50° C and most preferably at approximately room temperature.

The examples shown herein are illustrative of the method of preparation of both intermediates and compounds of the invention.

Specific compound preparation and herbicidal activity of the compounds of this invention are shown in the following examples.

EXAMPLE I

N-METHYL-N(CARBOXYMETHYLTHIOMETHYL) AMINE HYDROCHLORIDE (Intermediate)

300 milliliters of acetonitrile and 12.9 grams (0.1 mole) of 1,3,5-trimethylhexahydro-s-triazine were placed into a 500 milliliter 3-neck round bottom flask equipped with a stirrer, thermometer and dropping funnel. The mixture was stirred and cooled to $-30°C$ with a dry ice and acetone bath. 12 grams of HCl gas were added. Then 27.6 grams (0.3 mole) of mercapto acetic acid dissolved in 50 milliliters of acetonitrile was slowly added over a period of 15 minutes with stirring. The mixture was allowed to warm to room temperature and stand overnight with continued stirring.

The following day the solvent was removed invacuo. The product was then crystallized by addition of 500 milliliters of cold diethylether. The solid product was collected by filtration, washed with 200 milliliters of diethylether and dried in a vacuum dessicator. A yield of 40.6 grams (78.9% of theory) of the title compound is obtained. The structure was confirmed to be N-methyl-N(carboxymethylthiomethyl) amine hydro-chloride by Infrared and Nuclear Magnetic Resonance spectrums.

EXAMPLE II

1-METHYL-1-(N-PHENYLACETAMIDOTHIOMETHYL)3-PHENYL UREA 5 grams (0.029 mole) of the compound prepared in Example I, 6.94 grams (0.058 mole) of phenyl isocyanate and 100 milliliters of acetonitrile were combined in a 250 milliliter Erlenmeyer flask. The mixture was magnetically stirred and 2.95 grams (0.029) mole of triethylamine was then added. The resulting mixture was stirred and reacted at room temperature for one hour and then poured into 300 milliliters of ice water. The ice water and product mixture was then extracted with two 150 milliliter portions of benzene. The benzene extracts were combined, dried with $MgSO_4$, filtered and stripped of benzene invacuo. A yield of 6.6 grams (61% of theory) of the title compound was obtained. The structure was confirmed by Nuclear Magnetic Resonance spectrum. The $n_D^{30}$ was 1.5533. This compound will be referred to as compound 1.

EXAMPLE III

1-METHYL-1-[N-(4-CHLOROPHENYL)ACETAMIDOTHIOMETHYL]3-(4-CHLOROPHENYL) UREA

This example was prepared in the same type of equipment and in the same manner as Example II with the exceptions that 5 grams (0.029 mole) of the compound prepared in Example I was reacted with 8.95 grams (0.058 mole) of 4-chlorophenylisocyanate in the presence of 2.95 grams (0.029 mole) of triethylamine and 100 milliliters of acetonitrile. The yield was 4.4 grams (34.3% of theory) of the title compound. The structure was confirmed by Nuclear Magnetic Resonance spectrum. The $n_D^{30}$ was 1.5554. This compound will be referred to as compound 2.

EXAMPLE IV

1-METHYL-1-[N-(3,4-DICHLOROPHENYL)ACETAMIDOTHIOMETHYL]3-(3,4-DICHLOROPHENYL)UREA

In the same manner as Example Ii, 5 grams (0.029 mole) of Example I, 10.9 grams (0.058 mole) of 3,4-dichlorophenylisocyanate, 2.95 grams (0.029 mole) of triethylamine and 100 milliliters of acetonitrile were combined to yield 9.4 grams (63.4% of theory) of the title compound. The structure was confirmed by Nuclear Magnetic Resonance spectrum. Compound had characteristics of glass. This compound will be referred to as compound 3.

In the following table, the above four examples are listed together with three additional examples which were prepared in a manner analogous to that described above, starting with the appropriate materials. The compounds in the table are representative of those embodied in the present invention.

TABLE I $$Y-\text{(C}_6\text{H}_3\text{X)}-NHC(=O)-CH_2SCH_2N(CH_3)C(=O)NH-\text{(C}_6\text{H}_3\text{X)}-Y$$

| Compound Number | X | Y | Physical Properties |
|---|---|---|---|
| 1 | hydrogen | hydrogen | $n_D^{30}$ 1.5533 |
| 2 | hydrogen | chlorine | $n_D^{30}$ 1.5554 |
| 3 | chlorine | chlorine | glass |
| 4 | CF$_3$ | hydrogen | $n_D^{30}$ 1.4986 |
| 5 | chlorine | hydrogen | $n_D^{30}$ 1.5745 |
| 6 | chlorine | CH$_3$ | m.p. 99 – 102° C |
| 7 | CF$_3$ | chlorine | $n_D^{30}$ 1.5174 |

Herbicidal Screening Test

As previously mentioned, the novel phenoxyalkylamides herein described are phytotoxic compounds which are useful and valuable in controlling various plant species. compounds of this invention are tested in herbicides in the following manner.

Pre-Emergence Herbicide Screening Test

Using an analytical balance, 20 milligrams of the compound to be tested is weighed out on a piece of glassine weighing paper. The paper and compound are placed in a 30 milliliter wide-mouth bottle and 3 milliliters of acetone containing 1% Tween 20 ®(an emulsifying agent defined as a polyoxyethylene sorbitan monolaurate) is added to dissolve the compound. If the material is not soluble in acetone, another solvent such as water, alcohol or dimethylformamide (DMF) is used instead. When dimethylformamide is used, only 0.5 milliliters or less is used to dissolve the compound and then another solvent is used to make up the volume up to 3 milliliters. The 3 milliliters of solution is sprayed uniformly on the soil contained in a shall Fiber flat one day after planting weed seeds in the flat of soil. A No. 152 DeVilbiss atomozer is used to apply the spray using compressed air at a pressure of 5 lb/sq. inches. The rate of application is 8 lb/acre and the spray volume is 143 gallons/acre.

On the date preceding treatment, the Fiber flat, which is 7 inches long, 5 inches wide, and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), yellow foxtail (*Setaria glauca*), redroot pigweed (*Amaranthus retroflexus*), Indian mustard (*Brassica juncea*), curly dock (*Rumex cruspus*), watergrass (*Echinochloa crusgalli*), and red oat (*Avena sativa*) . Ample seeds are planted to give about 20 to 50 seedlings per row after emergence depending on the size of the plants.

After treatment, the flats are placed in the greenhouse at a temperature of 70° to 85°F and watered by sprinkling. Two weeks after treatment the degree of injury or control is determined by comparison with untreated check plants of the same age. The injury rating from 0 to 100% is recorded for each species as percent control with 0% representing no injury and 100% representing complete injury.

Post-Emergency Herbicide Screening Test

Seeds of six plant species, including hairy crabgrass, watergrass, red oat, mustard, curly dock and Pinto beans (*Phaseolus vulgaris*) are planted in the Fiber flats as described above for pre-emergence screening. The flats are placed in the greenhouse at 70° to 85°F and watered daily with a sprinkler. About 10 to 14 days after planting when the primary leaves of the bean plants are almost fully expanded and the first trifoliate leaves are just starting to form, the plants are sprayed. The spray is prepared by weighing out 20 milligrams of the test compound, dissolving it in 5 milliliters of acetone containing 1% Tween 20 ®(an emulsifying agent defined as a polyoxyethylene sorbitan monolaurate) and then adding 5 milliliters of water. The solution is sprayed on the foliage using a No. 152 DeVilbiss atomizer at an air pressure of 5 lb/sq. inch. The spray concentration is 0.2 and the rate is 8 lb/acre. The spray volume is 476 gallons/acre. Injury ratings are recorded 14 days after treatment. The rating system is the same as described above in the pre-emergence test.

The results of these tests are shown in Table II.

TABLE II

| Compound Number | Percent Control* at 8 lb/A | |
|---|---|---|
| | Pre-Emergence | Post-Emergence |
| 1 | 49 | 75 |
| 2 | 91 | 92 |
| 3 | 87 | 100 |
| 4 | 67 | 100 |
| 5 | 39 | 83 |
| 6 | 10 | 88 |

TABLE II-continued

| Compound Number | Percent Control* at 8 lb/A | |
|---|---|---|
| | Pre-Emergence | Post-Emergence |
| 7 | 0 | 82 |

*Average for seven plant species in the pre-emergence test and for six plant species in the post-emergence test.

The compounds of the present invention are useful as herbicides in controlling the growth of undesirable vegetation by pre-emergence or post-emergence application to the locus where control is desired. The compounds are generally embodied in formulations suitable for convenient application. In general, such formulations will contain inert or occasionally active ingredients or diluent carriers in addition to the active compound. Examples of such ingredients or carriers are water, organic solvents, dust carriers, granular carriers, surface active agents, oil and water, water in oil emulsions, wetting agents, dispersing agents and emulsifying agents. The herbicidal formulations generally take the form of dusts, wettable powders, granules, solutions or emulsifiable concentrates.

Dusts are free-flowing powder compositions containing the herbicidal compound impregnated on a particulate carrier. The particle size of the carrier is usually in the range of from about 30 to 50 microns. Examples of suitable carriers are talc, bentonite, diatomaceous earth and pyrophyllite. Anticaking and antistatic agents can be added, if desired. The composition generally contains up to 50% of active ingredient.

Wettable powders are finely divided compositions comprising a particulate carrier impregnated with the herbicidal compound and additionally contain one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in *Pesticide Formulations* by Wade Van Valkenburg, Marcel Dekker, Inc., N.Y. 1973 at pages 79-84.

Granules comprise the herbicidal compound impregnated on a particulate inert carrier having a particle size of about 1 to 2 milliliters in diameter. The granules can be made by spraying a solution of the active ingredient in a volatile solvent onto the granular carrier. Suitable carriers in preparation of granules include clay, vermiculite, sawdust, granular carbon, and the like.

The herbicidal compounds can also be applied to the soil in the form of a solution in a suitable solvent. Solvents frequently used in herbiciedal formulations include kerosene, fuel oil, xylene, petroleum fractions with boiling ranges above xylene, and aromatic petroleum fractions rich in methylated napthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above, employing phytotoxic or herbicidally effective amounts of the compounds described herein, are applied to the loci where control is desired in any conventional manner. The loci referred to above include soil, seeds, seedlings and the actual plants. Dusts and liquid compositions can be applid by the use of power dusters, boom and hand sprayers and spray dusters. The compositions can also be applied from airplanes as dusts or sprays because they are effective in very low dosages. In order to modify or control growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition or irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvants or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenyoxyacetic acid, and the salts, esters and amides thereof; triazine derivatives, such as 2,4,-bis(3-methoxy-propalamino)-6-methyl-thio-s-triazine; 2-chloro-4-ethylamino-6-isopropylamino-s-triazine, and 2-ethylamino-4-isopropylamino-6-methyl-mercapto-s-triazine, urea derivatives such as 3-(3,4-dichlorophenyl)-1,1-dimethyl urea, and acetamides such as N,N-di-allyl-α-chloracetamide, N-(α-chloroacetyl) hexamethyleneamine, and N,N-diethyl-α-bromoacetamide, and the like; benzoic acids such as 3-amino-2,5-dichlorobenzoid; S-ethyl-dipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

The amount of a compound of the present invention which constitutes a phytotoxic or herbicidally effective amount depends upon the nature of the seeds or plants to be controlled. The rate of application of active ingredient varies from about 0.01 to about 50 pounds per acre, with the actual amount used depending on the overall cost and the desired results. It will be readily apparent to one skilled in the art that compounds exhibiting lower herbicidal activity will require a higher dosage rate for the same degree of control than more active compounds.

What is claimed is:

1. A compound having the formula

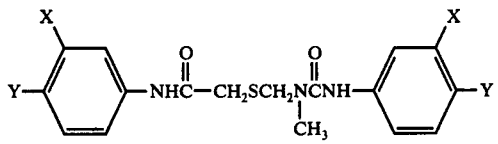

in which X and Y are identical or different and are independently selected from the group consisting of hydrogen, chlorine, $CH_3$ and $CF_3$.

2. The compound of claim 1 in which X and Y are identical.

3. The compound of claim 1 in which X is hydrogen and Y is hydrogen.

4. The compound of claim 1 in which X is hydrogen and Y is chlorine.

5. The compound of claim 1 in which X is chlorine and Y is chlorine.

6. The compound of claim 1 in which X is $CF_3$ and Y is hydrogen.

7. The compound of claim 1 in which X is chlorine and Y is hydrogen.

8. The compound of claim 1 in which X is chlorine and Y is $CH_3$.

9. The compound of claim 1 in which X is $CF_3$ and Y is chlorine.

10. A composition of matter comprising a herbicidally effective amount of the compound having the formula

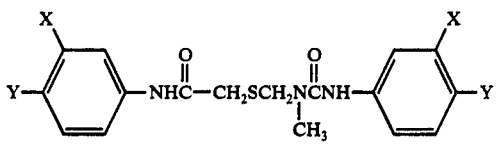

in which X and Y are identical or different and are independently selected from the group consisting of hydrogen, chlorine, $CH_3$ and $CF_3$ and an inert carrier.

11. The composition of claim 10 wherein X and Y are identical.

12. The composition of claim 10 wherein X is hydrogen and Y is hydrogen.

13. The composition of claim 10 wherein X is hydrogen and Y is chlorine.

14. The composition of claim 10 wherein X is chlorine and Y is chlorine.

15. The composition of claim 10 wherein X is $CF_3$ and Y is hydrogen.

16. The composition of claim 10 wherein X is chlorine and Y is hydrogen.

17. The composition of claim 10 wherein X is chlorine and Y is $CH_3$.

18. The composition of claim 10 wherein X is $CF_3$ and Y is chlorine.

19. A method of controlling undesirable vegetation comprising applying to the locus thereof a herbicidally effective amount of the compound having the formula

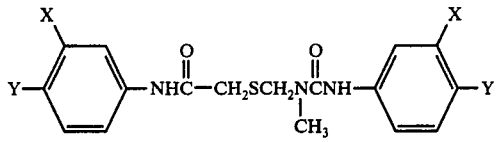

in which X and Y are identical or different and are independently selected from the group consisting of hydrogen, chlorine, $CH_3$ and $CF_3$.

20. The method of claim 19 wherein X and Y are identical.

21. The method of claim 19 wherein X is hydrogen and Y is hydrogen.

22. The method of claim 19 wherein X is hydrogen and Y is chlorine.

23. The method of claim 19 wherein X is chlorine and Y is chlorine.

24. The method of claim 19 wherein X is $CF_3$ and Y is hydrogen.

25. The method of claim 19 wherein X is chlorine and Y is hydrogen.

26. The method of claim 19 wherein X is chlorine and Y is $CH_3$.

27. The method of claim 19 wherein X is $CF_3$ and Y is chlorine.

* * * * *